United States Patent
Day et al.

(10) Patent No.: US 8,994,938 B2
(45) Date of Patent: Mar. 31, 2015

(54) RAMAN SPECTROSCOPY USING DIFFRACTIVE MEMS

(75) Inventors: David R. Day, Boxford, MA (US); Malcolm C. Smith, Winchester, MA (US); Peidong Wang, Carlisle, MA (US)

(73) Assignee: Thermo Scientific Portable Analytical Instruments Inc., Tewksbury, MA (US)

( * ) Notice: Subject to any disclaimer, the term of this patent is extended or adjusted under 35 U.S.C. 154(b) by 33 days.

(21) Appl. No.: 13/486,846

(22) Filed: Jun. 1, 2012

(65) Prior Publication Data
US 2013/0321799 A1    Dec. 5, 2013

(51) Int. Cl.
  *G01J 3/44* (2006.01)
  *G01J 3/02* (2006.01)
  *G01J 3/32* (2006.01)

(52) U.S. Cl.
  CPC ............... *G01J 3/32* (2013.01); *G01J 3/0229* (2013.01); *G01J 3/0272* (2013.01); *G01J 3/44* (2013.01)
  USPC ........................................................... 356/301

(58) Field of Classification Search
  USPC .............................................. 356/72–73, 301
  See application file for complete search history.

(56) References Cited

U.S. PATENT DOCUMENTS

| | | |
|---|---|---|
| 4,615,619 A | 10/1986 | Fateley |
| 4,799,795 A | 1/1989 | Fateley |
| 4,856,897 A | 8/1989 | Fateley et al. |
| 5,483,335 A | 1/1996 | Tobias |
| 5,485,268 A | 1/1996 | Tobias |
| 6,046,808 A | 4/2000 | Fateley |
| 6,128,078 A | 10/2000 | Fateley |
| 6,271,917 B1 | 8/2001 | Hagler |
| 6,392,748 B1 | 5/2002 | Fateley |
| 6,996,292 B1 | 2/2006 | Gentry et al. |
| 7,262,846 B2 | 8/2007 | Hagler |
| 2004/0218172 A1* | 11/2004 | DeVerse et al. ............... 356/300 |
| 2008/0174777 A1 | 7/2008 | Carron |

OTHER PUBLICATIONS

Deverse et al., "Realization of the Hadamard Multiplex Advantage Using a Programmable Optical Mask in a dispersive Flat-Field Near-Infrared Spectrometer," Applied Spectroscopy, vol. 54, No. 12, 2000, pp. 1751-1758.

Mende et al., "Hadamard Spectroscopy with a Two-Dimensional Detecting Array," Applied Optics, vol. 32, No. 34, 1993, pp. 7095-7105.

Tilotta et al., "A Visible Near-Infrared Hadamard Transform Spectrometer Based on a Liquid Crystal Spatial Light Modulator Array. A New Aproach in Spectrometry," Applied Spectroscopy, vol. 41, No. 5, 1987, pp. 727-734.

Tilotta et al., "Hadamard Transform Visible Raman Spectrometry," Applied Spectroscopy, vol. 41, No. 8, 1987, pp. 1280-1287.

(Continued)

*Primary Examiner* — Abdullahi Nur
(74) *Attorney, Agent, or Firm* — Ion C. Abraham

(57) ABSTRACT

A Raman spectrometer including a laser excitation source, edge filters, and detection optics that direct light into a spectrograph. A spectrograph containing a dispersive element and optics that directs various wavelengths of light onto a segmented diffractive MEMS light modulator array. The MEMS array, depending on actuation state, directs light either to or away from a single detector. Control electronics drive the MEMS light modulator for either sequential wavelength measurement or multiplexed wavelength measurement (Hadamard for example).

14 Claims, 6 Drawing Sheets

(56) References Cited

OTHER PUBLICATIONS

Tilotta et al., "Design and Performance of a Hadamard Transform Infrared Spectrometer with No Moving Parts," Applied Spectroscopy, vol. 49, No. 9, 1995, pp. 1338-1348.

Treado et al., "A Thousand Points of Light: The Hadamard Transform in Chemical Analysis and Instrumentation," Anal. Chem., vol. 61, No. 11, 1989, pp. 723A-734A.

Treado et al., "Multichannel Hadamard Transform Raman Microscopy," Applied Spectroscopy, vol. 44, No. 1, 1990, pp. 1-4.

Day, D.R. et al., "Diffractive-MEMS implementation of a Hadamard near-infrared spectrometer," Transducers '05, The 13th International Conference on Solid-state Sensors, Actuators and Microscopes. Digest of Technical Papers (IEEE Cat. No. 05TH8791) IEEE Pscataway, NJ, US, vol. 2, Jun. 2005, pp. 1246-1249.

Butler, M. et al., "Digital-transform spectroscopy shows its versatility." Laser Focus World, Pennwell, Tulsa, OK, US, vol. 41, No. 9, Sep. 1, 2005, pp. 82-85.

\* cited by examiner

RAMAN SPECTROSCOPY USING DIFFRACTIVE MEMS

BACKGROUND

Tremendous strides have been made to reduce the size of classic laboratory scientific analyzers. For some types of analyzers, e.g. Raman and infrared (IR) spectrometers, this has progressed to handheld, self powered instruments. These portable instruments now enable field use applications that were simply not possible in the past. Whereas handheld Raman spectrometers currently exist using standard silicon based detector arrays for visible and near IR sensing, some applications require even longer wavelength detector arrays, such as Indium Gallium Arsenide (InGaAs). These types of detector arrays are very expensive and require significant power for cooling. One prior art solution is to use a segmented optical modulator that has the ability to turn on or off selected wavelengths that are all directed to a single detector. The single detector is less expensive and requires little cooling power. Prior art has shown that spectrometers of this type can be implemented with optical light modulators based on micromirror arrays.

FIG. 1 illustrates a portable Raman spectrometer of the prior art. A laser source is filtered and then focused onto a sample. Inelastically scattered light from the sample is collected (eg. Stokes scattered light), passed through a filter that allows only wavelengths beyond that of the laser, and then directed to the entrance slit of a spectrometer. The spectrometer typically has an optical collimator (either a mirror or a lens) followed by a dispersive element (a grating or prism) where the incoming light is dispersed at different angles depending on the wavelength. The diverging but still collimated wavelengths are then focused (either by a lens or a mirror) on to a detector array e.g. a charge-coupled detector (CCD) array. Detector arrays are cost-effective in the visible range, up to 1.1 microns. In the near-IR range, the detectors are comparatively expensive.

FIG. 2 illustrates another prior art Raman spectrometer. The embodiment is similar to that shown in FIG. 1. In lieu of a detector array, a single detector is used. The dispersive element is tilted during the measurement to focus the wavelength of interest onto the single detector.

FIG. 3 illustrates another prior art Raman spectrometer. The embodiment is similar to that shown in FIG. 1. In lieu of a detector array, an array of micro-mirrors is used. Each micro-mirror in turn, reflects the wavelength of interest onto a single detector. The micro-mirror either reflects the light to or away from the detector. One wavelength or various combinations of wavelengths may be measured at a time.

SUMMARY OF INVENTION

The present invention is directed towards a Raman spectrometer assembly using a diffractive MEMS array as an effective optical wavelength modulator. The assembly includes a Raman spectrometer having typical excitation and light collection components, a spectrograph assembly that incorporates a segmented optical light modulator based on programmable diffractive MEMS pixels, and electronics to coordinate pixel actuation and detector signal monitoring.

In one measurement embodiment, the dispersed wavelengths are individually collected. Each diffractive pixel, in turn, directs the wavelength of interest onto a single detector while the wavelengths not of interest are diffracted away from the detector.

In another measurement embodiment, wavelengths from multiple pixels are collected at the same time. A sequence of pixel encodings, where each encoding is a pattern of "on" and "off" pixels, are programmed to the MEMS segmented light modulator and the signal is measured at the detector for each of said encodings. The measured spectrum is then calculated from mathematical manipulation of the detector readings.

In another embodiment a sequence of pixel encodings according to a Hadamard matrix are programmed to the MEMS segmented light modulator. A reverse Hadamard transform is applied to the measured data to retrieve the spectrum associated with the sample.

DETAILED DESCRIPTION

Figure 1:
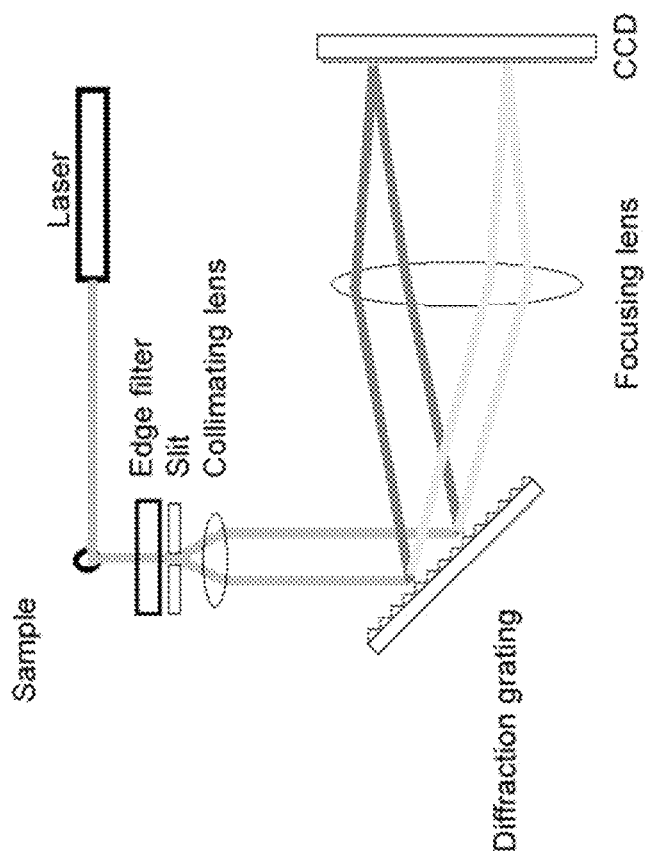
FIG. 1 illustrates a portable Raman spectrometer of the prior art.
Figure 2:
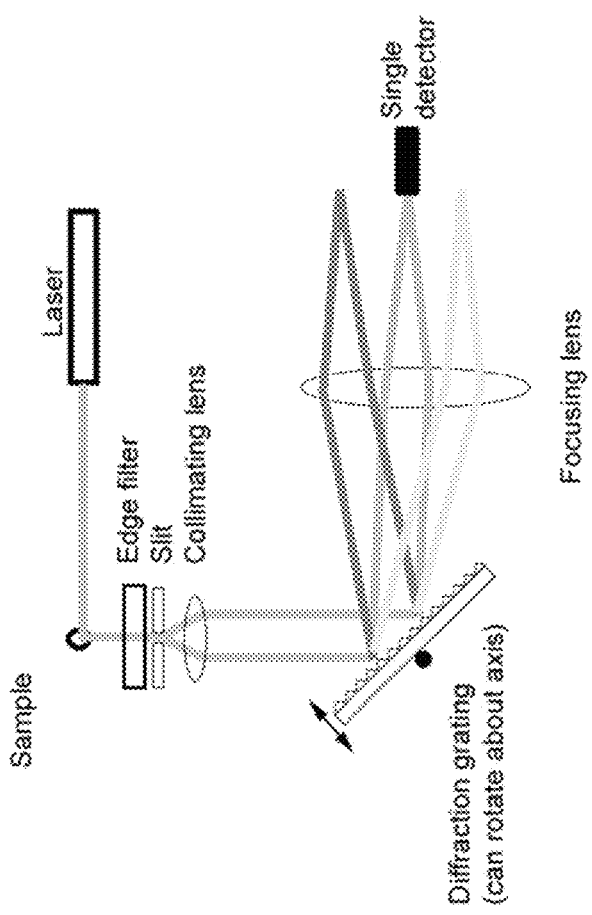
FIG. 2 illustrates another prior art Raman spectrometer.
Figure 3:
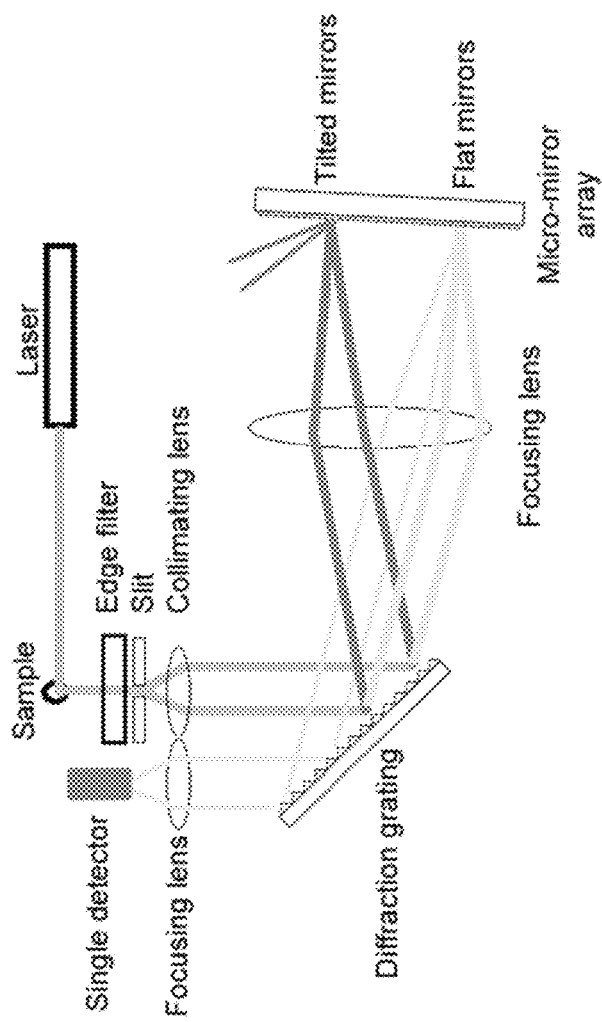
FIG. 3 illustrates another prior art Raman spectrometer.
Figure 4:
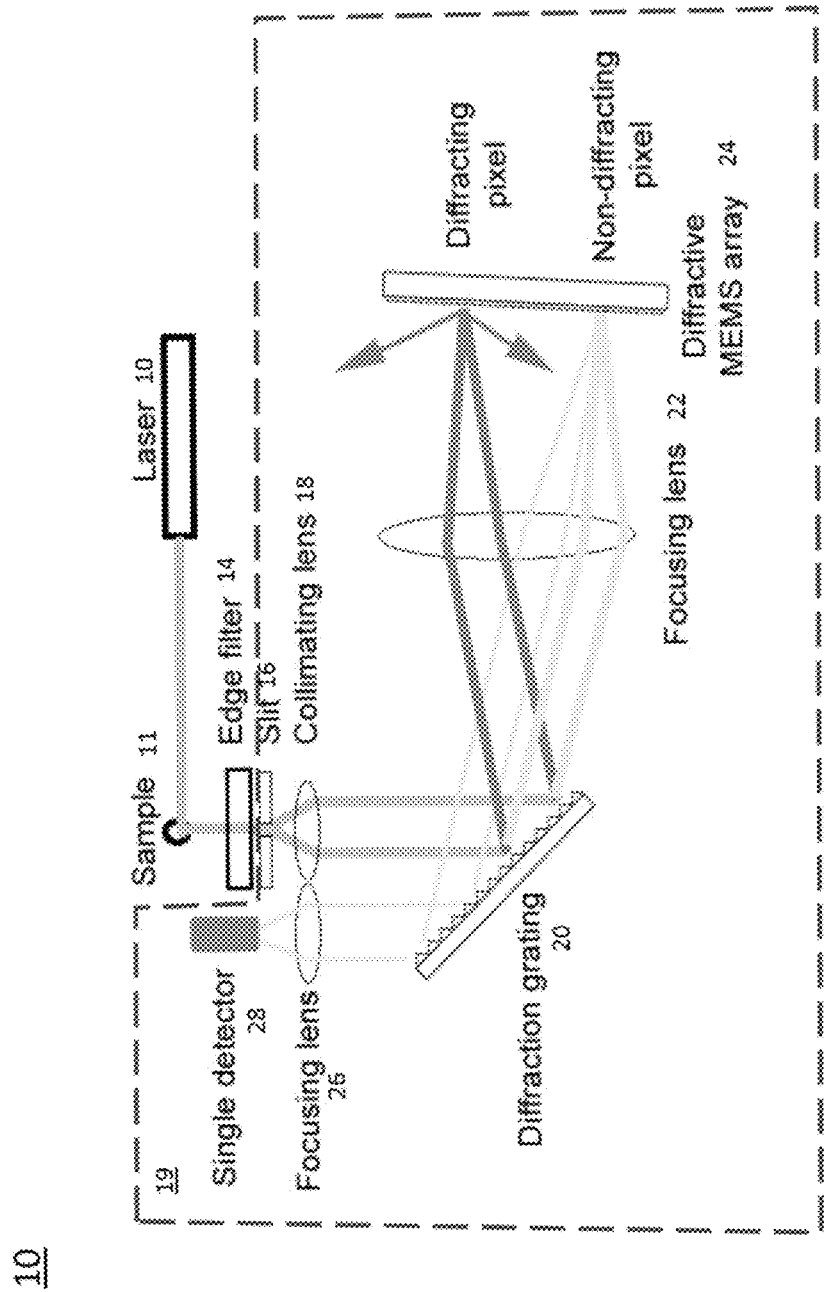
FIG. 4 illustrates a Raman spectrometer having a segmented diffractive light modulator according to the invention.

FIG. 4 illustrates a Raman instrument includes an excitation source 10, e.g. a laser, for exciting a sample 11. The resulting Stokes shifted signal from the sample passes through an edge filter 14 and enters the spectrograph.

For this illustrative embodiment of the spectrograph 19, the sample signal passes through a slit 16 and a collimating lens 18 before reflecting off a diffraction grating 20. The diffracted excitation signal passes through a first focusing lens 22 onto a diffractive MEMs array 24 to a segment, e.g. pixel, corresponding to the wavelength of interest. The portion of the sample signal solely containing the wavelength of interest passes through the first focusing lens 22, reflects off the diffraction grating 20, passes through a second focusing lens 26 onto a single detector 28. The diffractive MEMs array 24 and the detector 28 are connected to the controller (not shown).

The diffractive MEMS array 24 is a segmented light modulator with diffractive segments or pixels. In an unactuated state (ON), each pixel behaves like a flat mirror. When the pixel is actuated (OFF), a corrugated surface structure is created that acts as a diffraction grating. The light is reflected into diffractive orders such that little or no light is transmitted to the detector. Each pixel is associated with a unique wavelength. The collection of wavelength measurements from each pixel results in a spectrum of the sample under test.

The laser 10 may be within the operating wavelength range of 0.2-2 microns.

The detector 28 is a visible or near IR detector, e.g. InGaAs detector.

To be a practical "hand-held" instrument, the spectrometer should meet generally accepted ergonomic standards for such tools. Eastman Kodak's publication [Eastman Kodak Co. 1983, Ergonomic Design for People at Work, Lifetime Learning Pub., Belmont, Calif.] describes requirements for hand-held tools generally and includes a recommended maximum weight of five pounds for hand-held tools. Further, the size/volume of the tool should be small enough so that the tool is not cumbersome and unwieldy. The above-recommended maximum weight may also limit the power capacity of the tool, and consequently, the amount of time that the tool can operate. That is, the weight of a power source generally increases as its power rating increases, and in particular, the weight of battery power sources becomes quite large relative to the overall weight of the tool when large amounts of power are required for the tool's operation. As a result, the power consumption of the tool should be controlled to allow the tool to be used over an extended period of time (e.g., hours) with a relatively lightweight power source, for example, a battery power source that is light enough to be employed in a hand-held tool.

In practice, to be hand held and portable, a spectrometer should contain its own light source. Light sources, however, consume a considerable amount of power. Thus, the power consumption of both the control electronics and the light source are important considerations when developing a hand held spectrometer.

In operation, the laser excites samples under test to induce Raman light scattering. The scattered light is coupled to a spectrometer containing a fixed grating that disperses the various wavelengths across the segmented light modulator. The segmented light modulator, through electronic actuation, reflects selected wavelengths to a single detector. The spectrometer can be used to sequentially sample wavelengths or in a multiplex mode (e.g. Hadamard) to measure multiple wavelengths simultaneously. The spectrometer can be used in the UV, visible, or IR regions of the optical spectrum.

Figure 5:
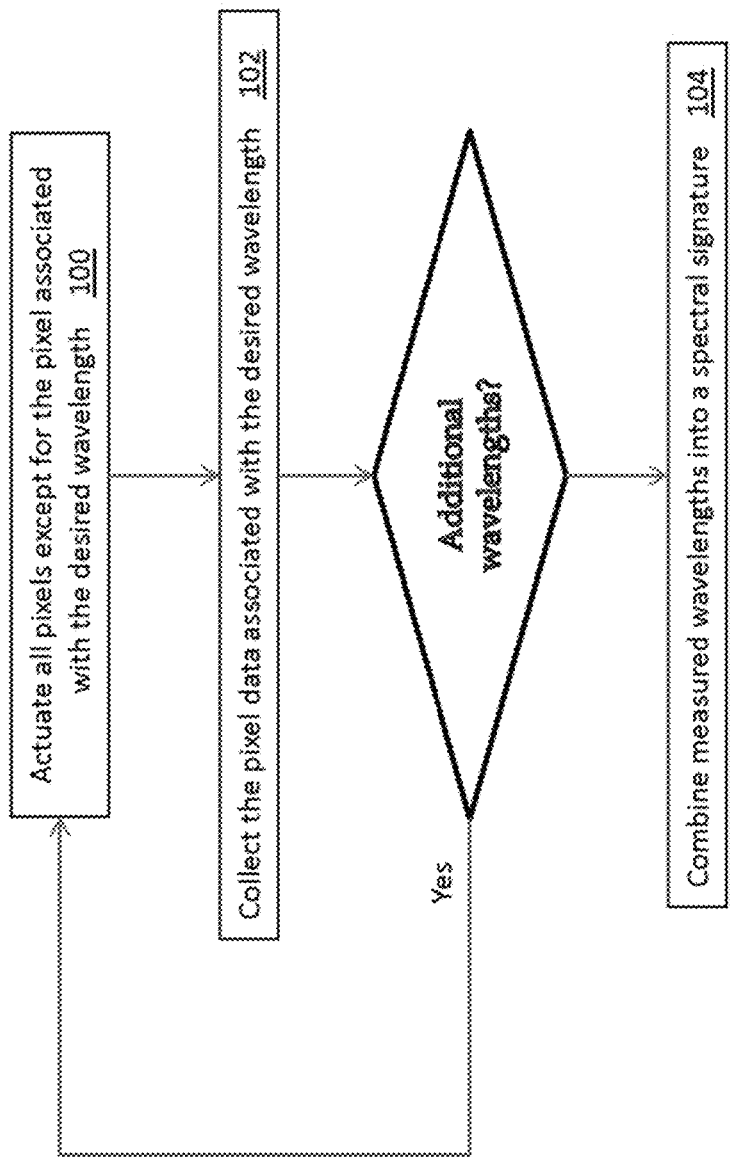
FIG. 5 illustrates a first process flowchart according to the invention. Each pixel is sequentially measured.

FIG. 5 illustrates a first process flowchart according to the sequential sample mode embodiment of the invention. In this embodiment, the dispersed wavelengths are individually collected. All pixels, except for one, are actuated for each sequence in the measurement (100). The wavelength associated with the single non-actuated pixel is reflected to the detector and measured (102). This sequence is repeated for all wavelengths (pixels) until the entire spectrum is complete (104).

Figure 6:
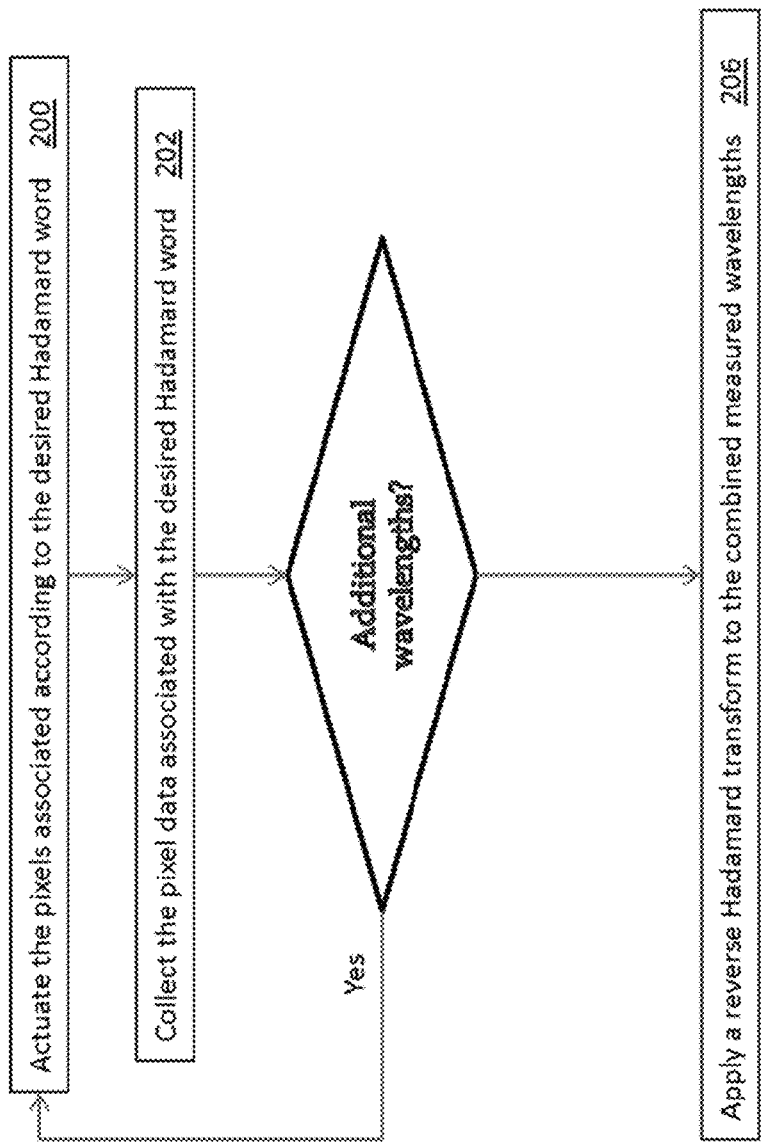
FIG. 6 illustrates a second process flowchart according to the invention. The pixels are measured according to a Hadamard encoding matrix.

FIG. 6 illustrates a second process flowchart according to the multiplex sample mode of the invention. In this measurement embodiment, the dispersed wavelengths are collected using Hadamard encoding. The diffractive pixels within the segmented light modulator collect data according to a Hadamard matrix. The measured data is a combination of different wavelengths. A reverse Hadamard transform is applied to the measured data to retrieve the spectrum associated with the sample.

A Hadamard matrix is a square matrix whose entries are +1 or −1 and whose rows are mutually orthogonal. Geometrically, this means that every two different rows a Hadamard matrix represents two perpendicular vectors. Combinatorially, it means that every two different rows have matching entries in exactly half of their columns and mismatched entries in the remaining columns. The corresponding properties hold for the columns as well as the rows.

For a given Hadamard matrix, the sampling may occur either by stepping through each column or each word. In step 200, actuate the segmented light modulator according to the desired Hadamard encoding where a 1 represents a reflective (flat) pixel and −1 would represent a diffractive pixel. In step 202, collect the pixel data according to the desired Hadamard word/encoding. Repeat steps 200 and 202, until all desired Hadmard encodings have been measured. In step 206, the combined measurements are transformed according to a reverse Hadamard transform into a spectral signature, e.g. Raman spectrum, indicative of the sample under test.

We claim:

1. A Raman spectrometer comprising:
an excitation source generating a Raman signal directly towards a sample;
a filter for receiving the Raman signal from the sample;
a spectrograph including,
a slit and lens for receiving the Raman signal from the filter,
a diffraction grating for dispersing the Raman signal,
a first optic for focusing the diffracted Raman signal on to a segmented diffractive MEMS array, each segment having two states,
a controller for providing control signals to the segmented diffractive MEMS array,
a second optic for collimating a portion of the diffracted Raman signal from the MEMS array to the diffraction grating,
the diffraction grating directing the Raman signal such that each segment in the MEMS array receives a different wavelength range of a Raman spectrum.

2. A Raman spectrometer, as in claim 1, wherein:
the controller sets a segment corresponding to a wavelength of interest to one of the two states to direct a portion of the Raman signal to a detector; and
the controller sets the remaining segments to the other of the two states to direct the remaining Raman signal away from the detector.

3. A Raman spectrometer, as in claim 1, wherein:
the controller sets multiple segments corresponding to multiple wavelengths of interest to one of the two states to direct a portion of the Raman signal to a detector; and
the controller sets the remaining segments to the other of the two states to direct the remaining Raman signal away from the detector.

4. A Raman spectrometer, as in claim 1, wherein:
the controller sets a segment corresponding to a wavelength of interest to one of the two states to direct a portion of the Raman signal to a detector,
the controller sets the remaining segments to the other of the two states to direct the Raman signal away from the detector, and
the controller receives a series of single segment measurements from the detector and combines the series to generate the corresponding Raman spectrum.

5. A Raman spectrometer, as in claim 1, wherein:
the controller sets multiple segments corresponding to multiple wavelengths of interest to one of the two states to direct a portion of the Raman signal to a detector,
the controller sets the remaining segments to the other of the two states to direct the Raman signal away from the detector, and
the controller receives a series of multiple segment measurements from the detector and applying a transform to the series to generate the corresponding Raman spectrum.

6. A Raman spectrometer, as in claim 5, wherein the multiple segments selected correspond to sequential rows or columns of a Hadamard matrix.

7. The Raman spectrometer of claim 1 wherein a detector receives the portion of the Raman signal corresponding to one of the two states.

8. A method comprising:
exciting a sample with a laser to generate a sample signal;
passing the excited sample signal through an edge filter;
passing the excited sample signal from the edge filter through a slit and collimating lens;
reflecting the passed signal off a diffraction grating;

passing the diffracted signal through a first focusing lens on to a diffracted MEMS array to a segment corresponding to a wavelength of interest;

passing the segment corresponding to the wavelength of interest through the first focusing lens;

reflecting the segment corresponding to the wavelength of interest off the diffraction grating; and passing the reflected segment corresponding to the wavelength of interest through a second focusing lens and on to a single detector.

9. The method of claim 8 wherein the diffractive MEMS array is a segmented light modulator with diffractive segments or pixels.

10. The method of claim 9 wherein each pixel is associated with a unique wavelength and a collection of wavelength measurements from each pixel results in a spectrum of a sample under test.

11. The method of claim 8 wherein the diffractive MEMs array and the detector 28 are connected to a controller.

12. The method of claim 11 wherein the controller provides control signals to the segmented diffractive MEMS array.

13. The method of claim 8 wherein the single detector is a visible or near infrared (IR) detector.

14. The method of claim 8 wherein the laser has an operating wavelength range of 0.2-2 microns.

\* \* \* \* \*